United States Patent [19]
Paludetto et al.

[11] Patent Number: 5,955,640
[45] Date of Patent: Sep. 21, 1999

[54] INTEGRATED PROCESS FOR THE PRODUCTION OF BUTENE-1

[75] Inventors: Renato Paludetto, Pioltello; Alfredo Orsi, Corsico; Roberto Trotta, Milan; Gianni Donati, Rho, all of Italy

[73] Assignees: Enichem S.p.A.; Snamprogetti S.p.A., both of Milan, Italy

[21] Appl. No.: 08/653,297

[22] Filed: May 24, 1996

[30] Foreign Application Priority Data

Jun. 30, 1995 [IT] Italy .................................. MI95A1400

[51] Int. Cl.$^6$ ........................... C07C 7/148; C07C 7/163; C10G 67/02
[52] U.S. Cl. .......................... 585/314; 585/258; 585/259; 585/315; 585/324; 585/664; 585/809; 585/820; 208/57
[58] Field of Search ...................................... 585/664, 310, 585/314, 315, 258, 259, 264, 809, 820, 324; 208/57

[56] References Cited

U.S. PATENT DOCUMENTS

| | | | |
|---|---|---|---|
| 4,513,153 | 4/1985 | Sandrin | 568/697 |
| 4,718,986 | 1/1988 | Comiotto et al. . | |
| 5,087,780 | 2/1992 | Arganbright | 585/259 |
| 5,338,889 | 8/1994 | Vora et al. | 568/697 |
| 5,365,011 | 11/1994 | Ramachandran et al. . | |
| 5,563,299 | 10/1996 | Paludetto et al. | 268/697 |

*Primary Examiner*—Bekir L. Yildirim
*Attorney, Agent, or Firm*—Nikaido, Marmelstein Murray & Oram LLP

[57] ABSTRACT

Integrated process for the production of butene-1 which comprises feeding a $C_4$ hydrocarbon stream to a separation unit of butene-1 and recycling the remaining stream to the same unit after treatment in a bond isomerization section to convert the remaining butenes-2 into butene-1, a molecular sieve separation unit is inserted in the cycle operating with the hydrocarbons in a vapour phase, for the purge of the paraffins.

20 Claims, 5 Drawing Sheets

INTEGRATED PROCESS FOR THE PRODUCTION OF BUTENE-1

The present invention relates to an integrated process for the production of butene-1.

More specifically the present invention relates to an integrated process for the production of butene-1 contained, together with the cis and trans butene-2 isomer in a $C_4$ stream.

Even more specifically, the present invention relates to the maximization of the use of the butene fraction in an integrated cycle for the production of butene-1.

Processes are known in the art for the recovery of butene-1 from mixtures containing it together with its cis and trans butene-2 isomers. U.S. Pat. No. 4,718,986, for example, describes a process for the separation of butene-1, contained in a $C_4$ stream of different origins, for example streams coming from steam cracking or catalytic cracking plants, using a suitable recovery unit. According to this patent, a $C_4$ stream, previously treated to eliminate the isobutene and butadiene and any possible acetylenic hydrocarbons, is fed to a recovery section of butene-1 consisting of a first distillation column from the top of which an isobutane fraction is recovered, containing, apart from isobutane, also considerable quantities of butene-1. The product at the bottom of the first column is fed to a second column from whose top butene-1 with a high purity (>99%) is recovered whereas a butane fraction is recovered from the bottom basically consisting of n-butane, cis and trans butene-2 and butene-1. Infact, the n-butane has an intermediate relative volatility between that of butene-1 and that of the cis and trans butene-2 isomers; its recovery consequently leads to the total loss of the butenes-2, as well as a certain quantity of butene-1.

According to this process therefore, the separation of the butene-1 is affected by significant losses of valuable material both in the purge at the top of the first distillation column and in that at the bottom of the second distillation column.

Another drawback relating to the process of the known art is that there is no utilization of the cis and trans butene-2 contained in the $C_4$ stream discharged, which must therefore be recovered separately.

The Applicants have now found a new process for the production of butene-1 from $C_4$ hydrocarbon streams, basically without isobutene, which overcomes the drawbacks of the known art. The present process, in fact, involves integrating the recovery section of butene-1 of the known art with a bond isomerization unit to transform the cis and trans butenes-2 contained in the purge streams into butene-1, and recycling the stream thus isomerized to the recovery section of butene-1.

However, as there would be an undesired accumulation of paraffins, n-butane and isobutane in an integrated process of this kind, a unit for the separation of the paraffins has been inserted in the cycle.

More specifically, purge streams leaving the recovery section of butene-1, containing paraffins and olefins are sent to a separation unit operating with zeolites in which a selective adsorption of the olefins is obtained. The olefins thus adsorbed can be recovered by desorption and then reinserted into the cycle. In this way it is possible to recover both the quantities of butene-1 and cis and trans butene-2 isomers, which would otherwise be lost in the purge streams.

This result can be efficiently obtained with reduced operating costs if the separation on molecular sieves is carried out in the vapour phase as operation in a liquid phase would produce unsatisfactory results owing to the required greater complexity of the plant.

The present invention therefore relates to an integrated process for the production of butene-1 which comprises:

a) feeding a fresh feed of a $C_4$ hydrocarbon stream, consisting essentially of linear butenes, butanes and, possibly, butadiene, as well as possible traces of acetylenic compounds, together with a recycled stream rich in butene-1 and containing possible traces of butadiene, to a selective hydrogenation section of butadiene and possible acetylenic compounds;

b) feeding the hydrogenated stream basically without butadiene and acetylenic compounds to a separation section of butene-1 to obtain a stream consisting of high purity butene-1 (>99%) and a remaining hydrocarbon stream consisting essentially of paraffins and olefins (butene-1 and butenes-2);

c) sending the remaining hydrocarbon stream, or a fraction thereof, in vapour phase, to a molecular sieve separation section for the separation of the paraffins (consisting essentially of butanes) from the olefins (consisting essentially of butenes 1 and 2), the recovery of the olefins and the purge of the paraffins;

d) sending the hydrocarbon stream containing the recovered olefins, together with the possible fraction not fed in step (c), to a bond isomerization section for the transformation of the cis and trans butenes-2 to butene 1;

e) recycling the isomerized stream to the selective hydrogenation section (a) after mixing with the fresh feed $C_4$ hydrocarbon stream.

An alternative integrated process for the production of butene-1 comprises:

a') feeding a fresh feed of a $C_4$ hydrocarbon stream, consisting essentially of linear butenes, butanes and, possibly, butadiene, as well as possible traces of acetylenic compounds, together with a recycled stream rich in butene-1 and containing possible traces of butadiene, to a selective hydrogenation section of butadiene and possible acetylenic compounds;

b') sending the hydrogenated hydrocarbon stream, or a fraction thereof, in vapour phase to a molecular sieve separation section for the separation of the paraffins (consisting essentially of butanes) from the olefins (consisting essentially of butenes 1 and 2), the recovery of the olefins and the purge of the paraffins;

c') sending the hydrocarbon stream containing the recovered olefins, together with the possible fraction not fed in step (b'), to a separation section of butene-1 to obtain a stream consisting of high purity butene-1 (>99%) and a remaining hydrocarbon stream consisting essentially of paraffins and olefins (butene-1 and butenes-2);

d') sending the remaining hydrocarbon stream to a bond isomerization section for the transformation of the cis and trans butenes-2 to butene-1;

e') recycling the isomerized stream to the selective hydrogenation section (a') after mixing with the fresh feed $C_4$ hydrocarbon stream.

The fresh feed of $C_4$ hydrocarbon stream used in the process of the present invention is basically without isobutene, as it comes, for example, from a plant for the production of methyl terbutyl ether (MTBE), and consists of isobutane, n-butane, butene-1, butene-2, trans and cis, butadiene and, possibly small quantities of acetylenic hydrocarbons and $C_3$ and/or $C_5$ hydrocarbons. This stream must be basically without isobutene which would otherwise pollute the end product of butene-1, as isobutene and butene-1 practically have the same boiling point.

More specifically, the isobutene is substantially eliminated from the fresh feed $C_4$ hydrocarbon stream, before being fed to the selective hydrogenation unit of step (a) or (a'), generally by means of an etherification unit in which an alkyl ter-butyl ether, for example methyl ter-butyl ether (MTBE) or an ethyl ter-butyl ether (ETBE) is produced, as disclosed in U.S. Pat. Nos. 3,979,461, 4,039,590, 4,071,567, 4,447,653, 4,465,870, 4,475,005, in U.K. patent 2,116,546 or in the published European patent application 470,655.

At the end of the treatments for the removal and/or elimination of the isobutene, the $C_4$ stream can approximately contain (in addition to a small quantity of $C_3$ and $C_5$ comprised, for example, between 0 and 5% by weight): 0.5–55% by weight of isobutane; 1–30% by weight of n-butane; 0–60% by weight of butadiene; the linear butenes being the complement to 100. The stream may also contain other components, at the level of 0–5,000 ppm, such as MTBE, ETBE, dimethylethers, terbutyl alcohol, methanol, ethanol, water, etc.

The selective hydrogenation section allows the elimination of the acetylenic compounds, possibly present in the fresh feed, and the transformation of the butadiene to linear butenes.

If neither the fresh feeding charge nor the recycled charge contain butadiene, the hydrogenation unit can be eliminated.

Any separation section of butene-1 can be used in the process of the present invention. For example, it is possible to operate with a fractional distillation unit, an extractive distillation unit or a unit operating by adsorption on molecular sieves. The fractional distillation unit is preferred, generally consisting of two distillation columns arranged in series. In a typical conformation, in the first column the separation at the top of the isobutane (isobutane stream) still present in the feeding stream is carried out whereas in the second column, fed with the bottom product of the first, butene-1 is obtained at the top with a purity of more than 99% and at the bottom a stream rich in residual n-butane, cis and trans butene-2, and containing butene-1 (butene stream). The operating conditions are described in U.S. Pat. No. 4,718,986 and in Canadian patent 1,232,919.

In an alternative configuration of the separation of butene-1 by fractional distillation, the position of the columns can be inverted. With this configuration in a first column the butene stream is discharged at the bottom whereas in the second column, fed with the top product of the first, the high purity butene-1 is obtained at the bottom, the isobutane (isobutane stream) being discharged at the top.

The molecular sieve separation section permits the elimination and the purge of the inert products, consisting of paraffinic hydrocarbons, basically n-butane and isobutane, from the cycle. The section can be fed either with the remaining hydrocarbon stream coming from the separation section of butene-1, consisting, for example, of the sum of the isobutane stream and butene stream, or with the stream leaving the hydrogenation section. In both cases it is possible to feed the total stream available or a fraction thereof of more than 5% by weight.

Any molecular sieve of the zeolitic type capable of having selectivity with respect to the double olefinic bond can be used in the process of the present invention. For example, compounds can be used corresponding to those having the general formula (I):

$$(Cat_{2/n}O)_x Me_2O_3 (SiO_2)_y \qquad (I)$$

wherein:
Cat represents a cation with a valence of "n", interchangeable with calcium (Ca), such as sodium, lithium, potassium, magnesium, etc;

x is a number between 0.7 and 1.5;
Me represents boron or aluminium; and
y is a number between 0.8 and 200, preferably between 1.3 and 4.

Zeolites of the X and Y type are preferred with a particle size of between 0.1 and 3 mm. These zeolites allow selectivity ratios olefins/paraffins of between 3 and 12 to be obtained, the selectivity being defined as:

$$S = \frac{R_o / P_o}{R_p / P_p}$$

wherein $R_o$ and $R_p$ are the adsorbed molar quantities of olefins (o) and paraffins (p) in equilibrium with the respective partial pressures $P_o$ and $P_p$ in the vapour.

The separation of the aliphatic hydrocarbons is carried out in a vapour phase at a temperature of between 20 and 180° C., preferably between 70 and 140° C., and a pressure of between 1 and 10 absolute bars, preferably between 1 and 5. To guarantee continuity of the process of the present invention, it is preferable to use a system of at least two sections arranged in parallel so that while one section is in the adsorption phase the other is in the desorption phase. The latter is carried out by elution of the olefins adsorbed on the molecular sieves with a desorbing agent, for example with aliphatic hydrocarbons, such as pentane, hexane, heptane, octane, etc. in vapour phase and subsequent rectification of the mixture obtained for the recovery of the olefins.

The molecular sieve separation section of the process of the present invention permits a purge stream of aliphatic hydrocarbons to be obtained practically without olefins or with a content of olefins of not more than 5% by weight.

In the isomerization section, fed with the olefinic stream which leaves the molecular sieve separation section or with the remaining hydrocarbon stream coming from the separation section of butene-1, the cis and trans butenes-2 are converted to butene-1. The isomerization reaction can be carried out, for example, with the process described in U.S. Pat. No. 4,814,542 using, as catalyst, a product based on alumina and metallic oxides.

At the outlet of the isomerization section a stream rich in butene-1 is obtained, possibly containing traces of butadiene, which is recycled to the selective hydrogenation section. Any possible $C_3-$ and $C_5+$ hydrocarbons formed in this phase, together with those possibly present in the fresh feed, are removed, for example by distillation.

If the separation section of butene-1 consists of a fractional distillation unit operating with two distillation columns arranged in series, the integrated process for the production of butene-1 may comprise the following operation steps:

i) feeding a fresh feed of a $C_4$ hydrocarbon stream, consisting essentially of linear butenes, butanes and, possibly, butadiene, as well as possible traces of acetylenic compounds, together with a recycled stream rich in butene-1 and containing possible traces of butadiene, to a selective hydrogenation section of butadiene and possible acetylenic compounds;

ii) sending the hydrogenated hydrocarbon stream, or a fraction thereof, in a vapour phase, to a molecular sieve separation section for the separation of the paraffins (consisting essentially of butanes) from the olefins (consisting essentially of butenes 1 and 2), the recovery of the olefins and the purge of the paraffins;

iii) sending the hydrocarbon stream containing the recovered olefins, together with the possible fraction not fed in step (ii), to a first column of a separation section of butene-1, the latter consisting of two distillation columns arranged in series;

iv) recycling the stream at the top of the first column of step (iii), consisting essentially of isobutane and butene-1, to the molecular sieve separation section (ii) whereas the stream at the bottom feeds the second distillation column;

v) discharging from the top of the second column a stream consisting essentially of high purity butene-1 (>99%) and sending the bottom stream of the second column, consisting essentially of butenes-2, to a bond isomerization section for the transformation of the cis and trans butenes-2 to butene-1;

vi) recycling the isomerized stream to the selective hydrogenation section (i) after mixing with the fresh feed $C_4$ hydrocarbon stream.

In an alternative configuration of the separation of butene-1 by fractional distillation, the position of the columns can be inverted. With this configuration, in a first column the butenic stream is discharged at the bottom whereas in the second column, fed with the bottom product of the first, the high purity butene-1 is taken from the bottom, the discharge of the isobutane (isobutane stream) taking place at the top. With this configuration the integrated process for the production of butene-1 can comprise the following operating steps:

I) feeding a fresh feed of a $C_4$ hydrocarbon stream, consisting essentially of linear butenes, butanes and, possibly, butadiene, as well as possible traces of acetylenic compounds, together with a recycled stream rich in butene-1 and containing possible traces of butadiene, to a selective hydrogenation section of butadiene and possible acetylenic compounds;

II) sending the hydrogenated hydrocarbon stream, or a fraction thereof, in a vapour phase to a molecular sieve separation section for the separation of the paraffins (consisting essentially of butanes) from the olefins (consisting essentially of butenes 1 and 2), the recovery of the olefins and purge of the paraffins;

III) sending the hydrocarbon stream containing the recovered olefins, together with the possible fraction not fed in step (II), to a first column of a separation section of butene-1, the latter consisting of two distillation columns arranged in series;

IV) sending the stream at the bottom of the first column of step (III), consisting essentially of butenes-2, to a bond isomerization section for the transformation of the cis and trans butenes-2 to butene-1 whereas the stream at the top feeds the second distillation column;

V) discharging from the bottom of the second column a stream consisting of high purity butene-1 (>99%) and sending the top stream of the second column, consisting essentially of isobutane and butene-1, to the molecular sieve separation section (II);

VI) recycling the isomerized stream to the selective hydrogenation section (I) after mixing with the fresh feed $C_4$ hydrocarbon stream.

BRIEF DESCRIPTION OF THE DRAWINGS

The integrated process for the production of butene-1 of the present invention can be better understood by referring to the block schemes of FIGS. 1–4 which represent an illustrative but not limiting embodiment thereof, and to the block scheme of FIG. 5 which represents an illustrative embodiment of the molecular sieve separation section alone.

DETAILED DESCRIPTION

Figure 1:
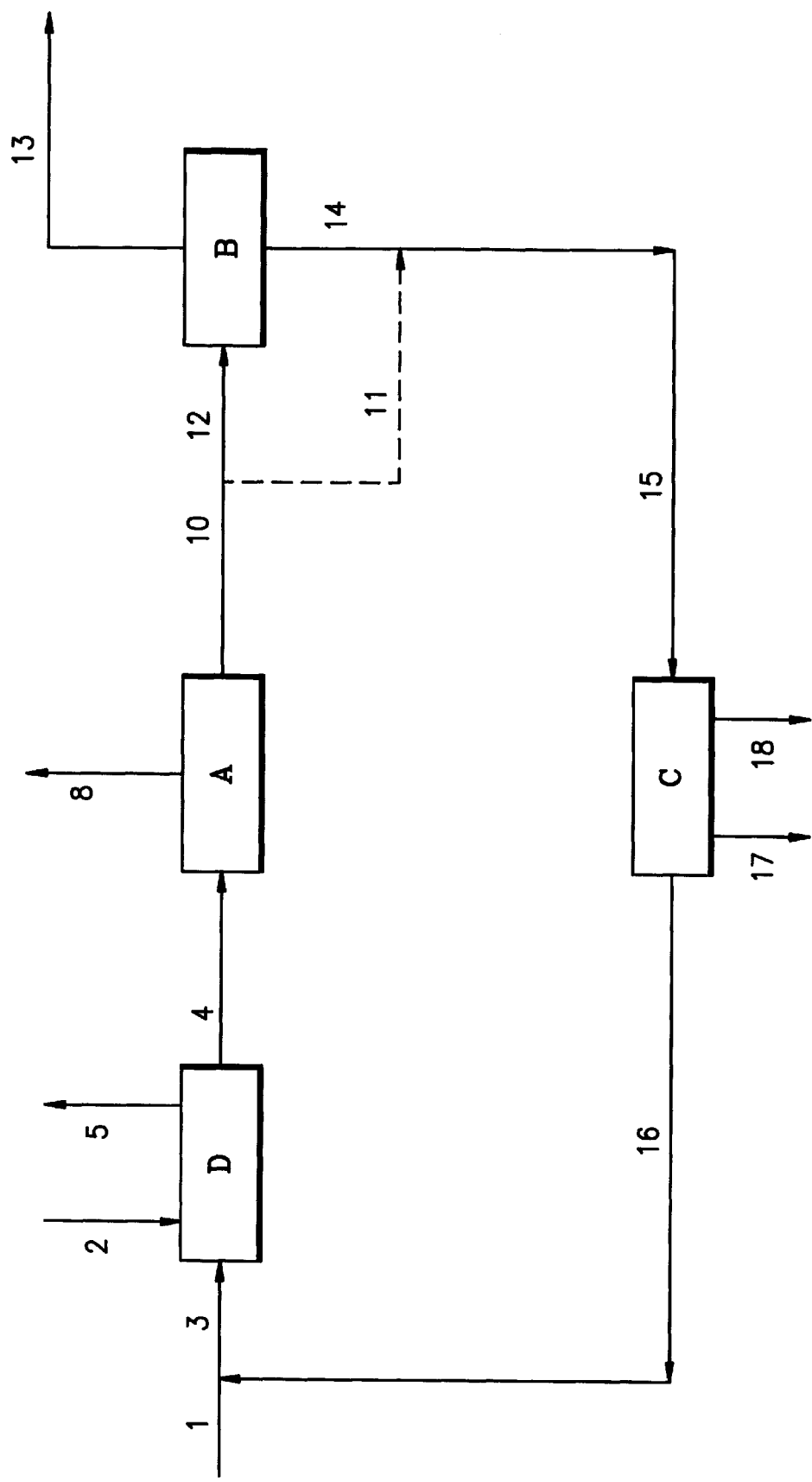

With reference to FIG. 1, A B, C and D respectively represent the separation section of butene-1 A, the molecular sieve separation section of the aliphatic hydrocarbons B, the bond isomerization section C and the selective hydrogenation section D. The stream (3), consisting of the sum of the $C_4$ hydrocarbon fraction (1) and the recycled fraction (16) coming from the isomerization unit C, is sent to the selective hydrogenation section D. Hydrogen (2) is fed to the same section. The unconverted hydrogen, if present, is purged with the stream (5).

The hydrogenated stream (4) is sent to the separation section of butene-1, A. When the butene-1 (8) has been recovered using the conventional methods not shown in the figure, for example those described in U.S. Pat. No. 4.718.986, the remaining hydrocarbon fraction (10) is sent, either totally or partially, to the molecular sieve separation section B. If there is a partial separation, part of the above residual fraction by-passes the separation section B, dashed line (11).

The paraffins (13) and the stream (14) consisting essentially of butene-1 and butene-2, cis and trans, and residual butanes are discharged from the separation section B. Stream (14), joined to the possible by-pass (11), forms the stream (15) which enters the isomerization section C. The stream (16) rich in butene-1 is extracted from this and recycled to the selective hydrogenation section D.

Any possible $C_3$- and $C_5$+ hydrocarbons formed during the isomerization or present in the $C_4$ feed (1), are discharged by means of (17) and (18).

Figure 2:
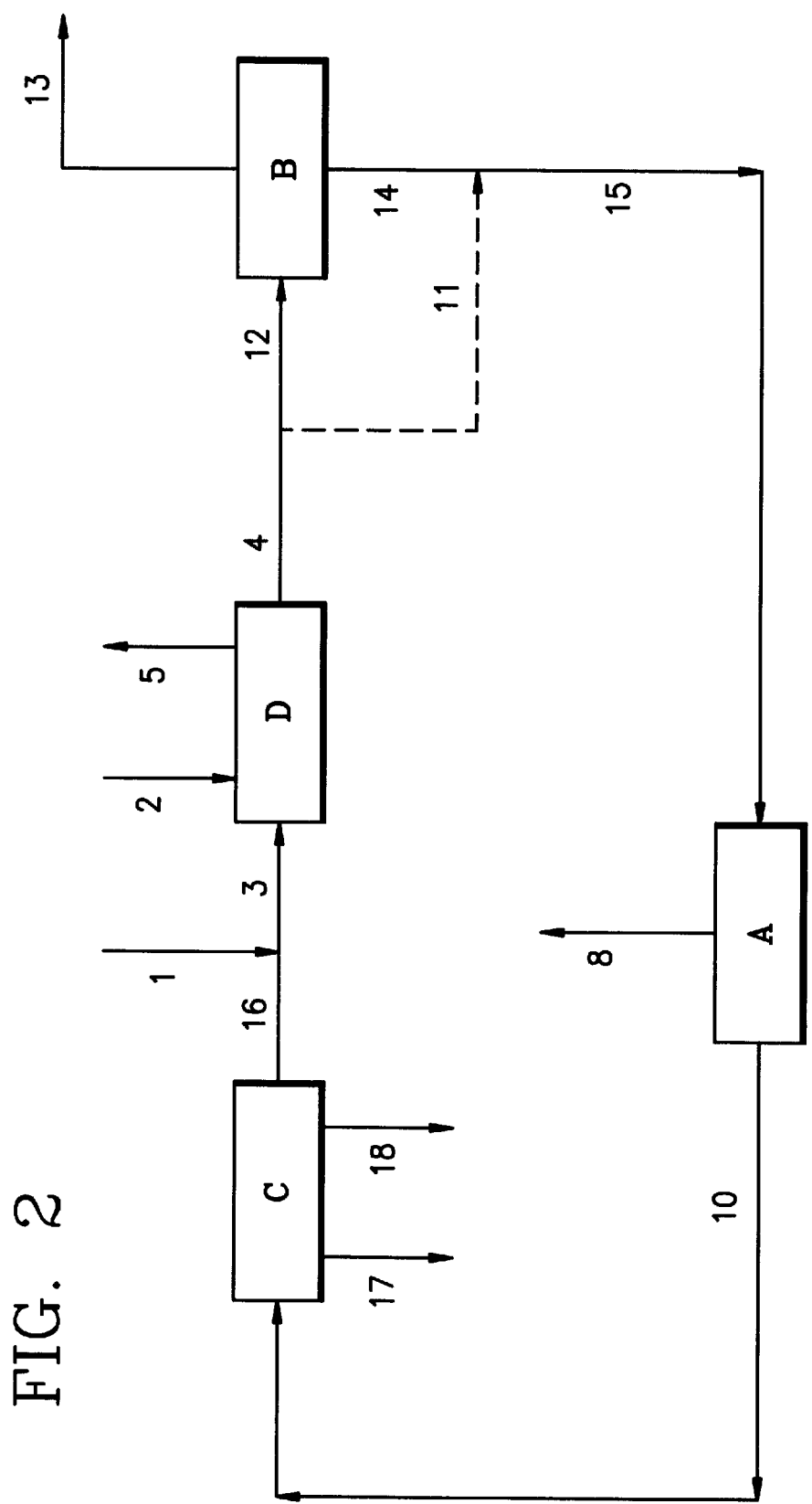

In FIG. 2 the separation section B is positioned upstream of the separation section of butene-1, A.

Figure 3:
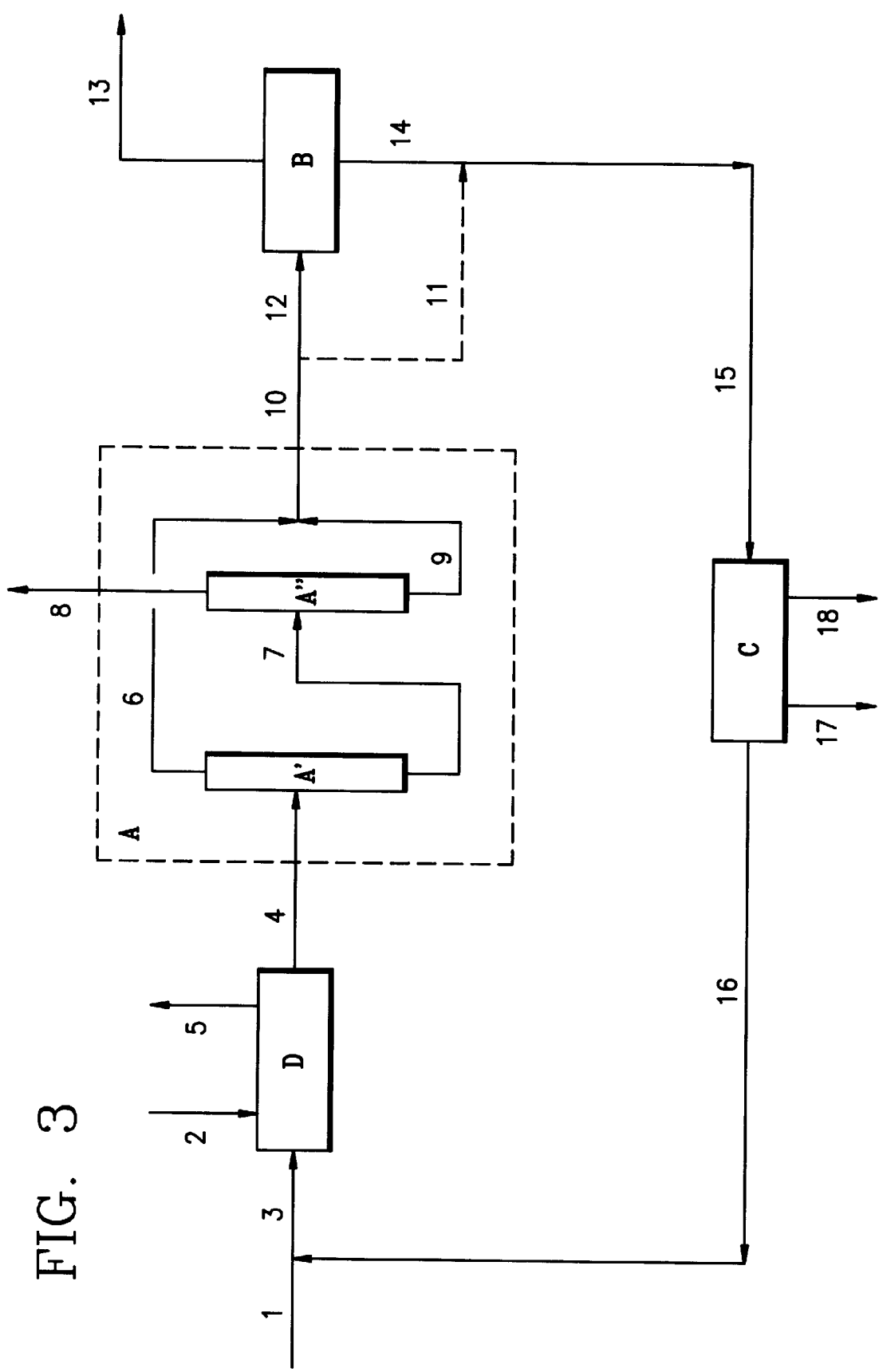

FIG. 3 is a development of FIG. 1 above, with an illustrative detail of section A. Section A consists of two distillation columns, A' and A". The first column A' is fed with the stream (4) coming from the selective hydrogenation and produces a stream at the top consisting essentially of isobutane. The second column, A", fed with the bottom stream (7) of the first column, produces, at the top, high purity butene-1 (>99%), stream (8), and at the bottom stream (9) consisting essentially of butenes-2 and n-butane.

Stream (6) and stream (9), joined in (10), are fed to the molecular sieve separation section B.

Figure 4:
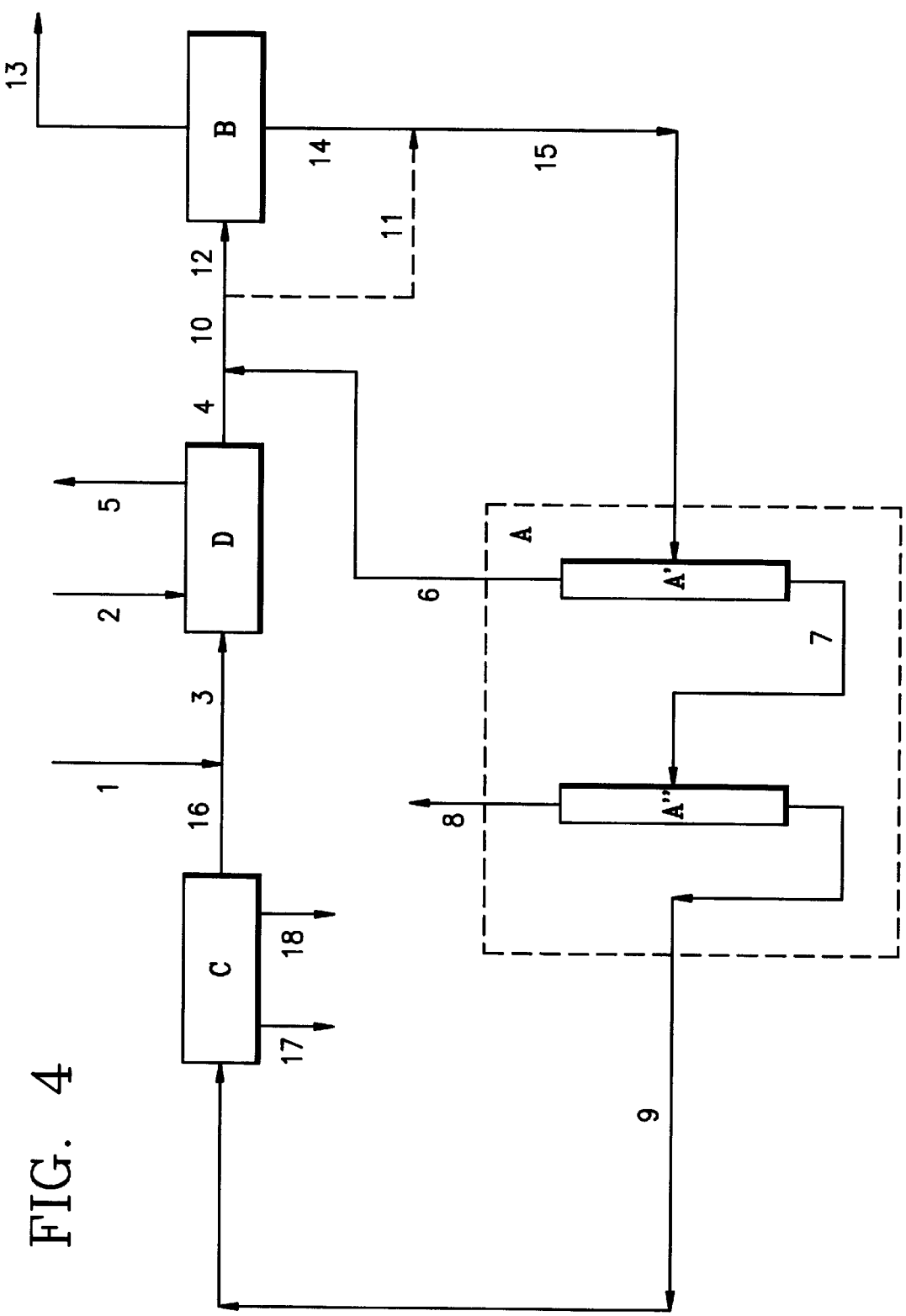

FIG. 4 is a development of FIG. 2 above with a variation in section A. In fact, in this configuration, the remaining hydrocarbon fraction which leaves section A, is not totally fed to the isomerization section C. In particular, the isobutane stream (6), leaving the top of column A', is recycled to the molecular sieve separation section B, whereas stream (9) alone, leaving the bottom of column A", is sent to the isomerization section C.

Figure 5:
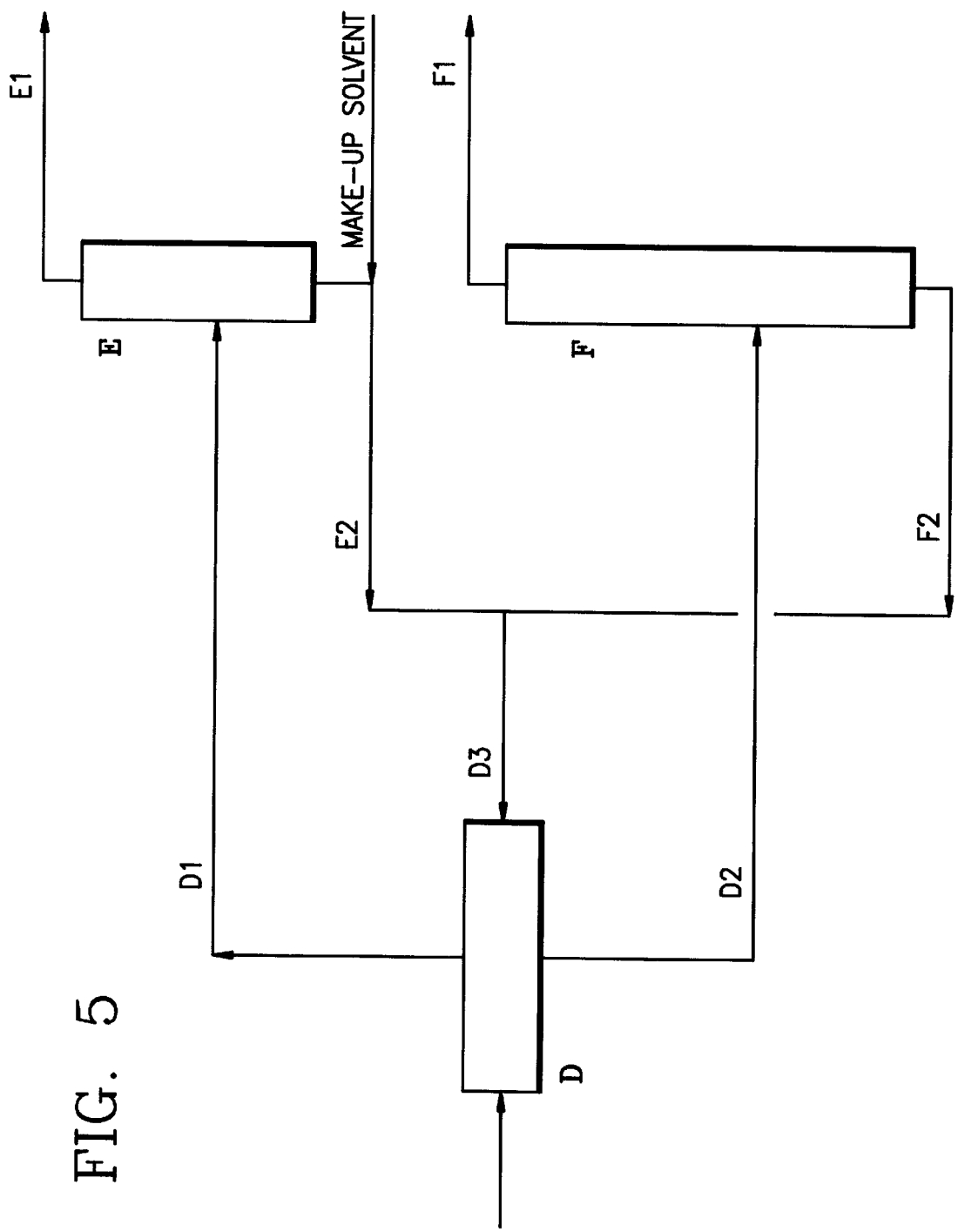

With reference to FIG. 5, the separation section B comprises an adsorption/desorption unit D and two distillation columns E and F.

To operate in continuous it is also possible to have two units D operating alternatively one in the adsorption phase and the other in the desorption phase.

Two streams D1 and D2 are recovered from unit D.

In the adsorption phase the stream D1 is recovered, practically without olefins, which is sent to the distillation column E for the recovery of the desorbing agent E2, which is recycled, from the purge butanic fraction E1.

In the desorption phase the olefinic fraction D2 is recovered and sent to the distillation column F for the recovery of the butene fraction F1 (readmitted to the cycle) from the desorbing agent F2 which is recycled to D.

The process of the present invention permits the purge, in an integrated process for the production of butene-1, of a paraffinic stream practically without olefins. It therefore permits an almost integral use of the olefins available thus maximizing the production of butene-1. In addition it reduces the concentration of the paraffins in the cycle and thus reducing investment costs and energy consumption.

Some illustrative but not limiting examples are given below to provide a better understanding of the present invention and to enable its embodiment.

EXAMPLE 1

With reference to the enclosed scheme of FIG. 3 and to the relative table 1 with the process quantifications for a capacity of about 730 g/h of butene-1, a $C_4$ hydrocarbon stream (1) is fed, having a flow rate of about 1120 g/h and the following composition:

|  | weight % |
|---|---|
| $C_3=$ | 0.03 |
| i-butene = | 0.06 |
| butene-1 = | 37.61 |
| butene-2-trans = | 20.70 |
| butene-2-cis = | 16.77 |
| isobutane = | 4.89 |
| n-butane = | 17.78 |
| butadiene = | 1.71 |
| acetylenic products = | 0.45 |

This stream is joined to the recycled stream (16) having a flow rate of about 2930 g/hr. The resulting stream (3) is fed to the hydrogenation section of butadiene D in which the butadiene is almost totally converted into linear butenes, a small part being converted into n-butane. The acetylenic compounds are also substantially hydrogenated in this section. The hydrogenated stream (4) is fed to the recovery section of butene-1 (A). In the configuration of FIG. 3, the stream (4) is fed to a first distillation column A1' where about 240 g/hr is obtained at the top of the isobutane stream (6), consisting essentially of all the isobutane, all the $C_3$ hydrocarbons contained. in the stream (4) and butene-1, as well as, naturally smaller quantities of n-butane and butenes-2.

The stream (7), basically without isobutane, is fed to column A"from which about 730 g/hr of butene-1 with a purity of more than 99% are obtained as top product (8). The stream (9) is joined to the stream (6), forming stream (10) fed to the molecular sieve separation section. Stream (10) contains about 20% by weight of paraffins. Of this stream about 30% (11) is by-passed whereas the remaining portion of the stream (12) goes to section B which operates at 130° C. and 4 bars of pressure. About 4000 cc of zeolite X are used as molecular sieves, in the form of ¹⁄₁₆" extruded pellets whereas n-hexane in a vapour phase (about 5000 g/hr) is used as a desorbing agent of the adsorbed olefins. After separation by distillation of the desorbing agent, a stream (13) consisting essentially of 288 g/hr of aliphatic hydrocarbons with a title of paraffins of about 96.6% is purged. In the stream (15) the content of aliphatic hydrocarbons is reduced to about 13% by weight. This stream is then fed to the bond isomerization section C in which there is a conversion of butenes-2 to butene-1 and other products belonging to the groups $C_3-$ and $C_5+$. These by-products are eliminated in (17) and (18) and the resulting fraction (16) is recycled to the hydrogenation section D.

EXAMPLE 2

The same procedure is carried out as in example 1 but referring to the sketch of FIG. 4 and process quantifications shown in table 2.

TABLE 1

| | Stream | | | | | | | | | | | |
|---|---|---|---|---|---|---|---|---|---|---|---|---|
| | 1 | | 2 | | 3 | | 4 | | 5 | | 6 | |
| | g/hr | % wt | g/hr | % wt | g/hr | % wt | g/hr | % wt | g/hr | % wt | g/hr | % wt |
| Hydrogen | 0.00 | 0.00 | 2.86 | 70.48 | 0.00 | 0.00 | 0.00 | 0.00 | 0.26 | 0.28 | 0.00 | 0.00 |
| C3 | 0.38 | 0.03 | 1.20 | 29.52 | 0.70 | 0.02 | 0.64 | 0.02 | 1.27 | 1.39 | 0.64 | 0.27 |
| Isobutane | 54.75 | 4.89 | 0.00 | 0.00 | 120.66 | 2.98 | 116.16 | 2.93 | 4.50 | 4.93 | 115.88 | 48.47 |
| Isobutene | 0.68 | 0.06 | 0.00 | 0.00 | 2.03 | 0.05 | 1.97 | 0.05 | 0.06 | 0.07 | 0.27 | 0.11 |
| Butene-1 | 421.09 | 37.61 | 0.00 | 0.00 | 1105.78 | 27.30 | 1047.22 | 26.42 | 30.28 | 33.16 | 100.26 | 41.94 |
| Butadiene | 19.14 | 1.71 | 0.00 | 0.00 | 21.77 | 0.54 | 0.24 | 0.01 | 0.00 | 0.00 | 0.03 | 0.01 |
| n-butane | 199.00 | 17.78 | 0.00 | 0.00 | 516.36 | 12.75 | 550.55 | 13.89 | 12.79 | 14.01 | 7.25 | 3.03 |
| t-butene-2 | 231.69 | 20.70 | 0.00 | 0.00 | 1375.01 | 33.95 | 1351.52 | 34.10 | 28.71 | 31.44 | 11.33 | 4.74 |
| c-butene-2 | 187.73 | 16.77 | 0.00 | 0.00 | 903.05 | 22.29 | 894.88 | 22.58 | 13.44 | 14.72 | 3.39 | 1.42 |
| C5+ | 0.00 | 0.00 | 0.00 | 0.00 | 0.00 | 0.00 | 0.00 | 0.00 | 0.00 | 0.00 | 0.00 | 0.00 |
| Acetilenics | 5.06 | 0.45 | 0.00 | 0.00 | 5.10 | 0.13 | 0.04 | 0.00 | 0.00 | 0.00 | 0.00 | 0.00 |
| Total | 1119.52 | 100.00 | 4.06 | 100.00 | 4050.46 | 100.00 | 3963.22 | 100.00 | 91.30 | 100.00 | 239.05 | 100.00 |

| | Stream | | | | | | | | | | | |
|---|---|---|---|---|---|---|---|---|---|---|---|---|
| | 7 | | 8 | | 9 | | 10 | | 11 | | 12 | |
| | g/hr | % wt | g/hr | % wt | g/hr | % wt | g/hr | % wt | g/hr | % wt | g/hr | % wt |
| Hydrogen | 0.00 | 0.00 | 0.00 | 0.00 | 0.00 | 0.00 | 0.00 | 0.00 | 0.00 | 0.00 | 0.00 | 0.00 |
| C3 | 0.00 | 0.00 | 0.00 | 0.00 | 0.00 | 0.00 | 0.64 | 0.02 | 0.19 | 0.02 | 0.44 | 0.02 |
| Isobutane | 0.29 | 0.01 | 0.29 | 0.04 | 0.00 | 0.00 | 115.88 | 3.58 | 34.76 | 3.58 | 81.11 | 3.58 |
| Isobutene | 1.70 | 0.05 | 1.56 | 0.21 | 0.15 | 0.00 | 0.42 | 0.01 | 0.13 | 0.01 | 0.29 | 0.01 |
| Butene-1 | 946.96 | 25.43 | 724.61 | 99.22 | 222.35 | 7.43 | 322.60 | 9.98 | 96.78 | 9.98 | 225.82 | 9.98 |
| Butadiene | 0.21 | 0.01 | 0.17 | 0.02 | 0.03 | 0.00 | 0.07 | 0.00 | 0.02 | 0.00 | 0.05 | 0.00 |

TABLE 1-continued

| | | | | | | | | | | | |
|---|---|---|---|---|---|---|---|---|---|---|---|
| n-butane | 543.30 | 14.59 | 2.12 | 0.29 | 541.18 | 18.08 | 548.43 | 16.96 | 164.53 | 16.96 | 383.90 | 16.96 |
| t-butene-2 | 1340.19 | 35.99 | 1.55 | 0.21 | 1338.63 | 44.71 | 1349.96 | 41.76 | 404.99 | 41.76 | 944.97 | 41.76 |
| c-butene-2 | 891.49 | 23.94 | 0.00 | 0.00 | 891.49 | 29.78 | 894.88 | 27.68 | 268.46 | 27.68 | 626.42 | 27.68 |
| C5+ | 0.00 | 0.00 | 0.00 | 0.00 | 0.00 | 0.00 | 0.00 | 0.00 | 0.00 | 0.00 | 0.00 | 0.00 |
| Acetilenics | 0.04 | 0.00 | 0.00 | 0.00 | 0.04 | 0.00 | 0.04 | 0.00 | 0.01 | 0.00 | 0.03 | 0.00 |
| Total | 3724.18 | 100.00 | 730.31 | 100.00 | 2993.87 | 100.00 | 3232.92 | 100.00 | 969.87 | 100.00 | 2263.04 | 100.00 |

| | Stream | | | | | | | | | | | |
|---|---|---|---|---|---|---|---|---|---|---|---|---|
| | 13 | | 14 | | 15 | | 16 | | 17 | | 18 | |
| | g/hr | % wt | g/hr | % wt | g/hr | % wt | g/hr | % wt | g/hr | % wt | g/hr | % wt |
| Hydrogen | 0.00 | 0.00 | 0.00 | 0.00 | 0.00 | 0.00 | 0.00 | 0.00 | 0.00 | 0.00 | 0.00 | 0.00 |
| C3 | 0.27 | 0.09 | 0.18 | 0.01 | 0.37 | 0.01 | 0.32 | 0.01 | 0.04 | 0.63 | 0.00 | 0.00 |
| Isobutane | 48.67 | 16.85 | 32.45 | 1.64 | 67.21 | 2.28 | 65.91 | 2.25 | 1.29 | 18.49 | 0.00 | 0.00 |
| Isobutene | 0.00 | 0.00 | 0.29 | 0.01 | 0.42 | 0.01 | 1.35 | 0.05 | 0.01 | 0.13 | 0.00 | 0.01 |
| Butene-1 | 1.19 | 0.41 | 224.63 | 11.38 | 321.41 | 10.92 | 684.69 | 23.36 | 4.74 | 67.76 | 0.19 | 3.06 |
| Butadiene | 0.00 | 0.00 | 0.05 | 0.00 | 0.07 | 0.00 | 2.63 | 0.09 | 0.00 | 0.00 | 0.00 | 0.00 |
| p-butane | 230.34 | 79.77 | 153.56 | 7.78 | 318.09 | 10.80 | 317.36 | 10.83 | 0.27 | 3.82 | 0.46 | 7.42 |
| t-butene-2 | 4.98 | 1.73 | 939.99 | 47.61 | 1344.98 | 45.68 | 1143.32 | 39.01 | 0.49 | 7.02 | 2.61 | 41.95 |
| c-butene-2 | 3.30 | 1.14 | 623.12 | 31.56 | 891.58 | 30.28 | 715.32 | 24.41 | 0.15 | 2.15 | 2.65 | 42.62 |
| C5+ | 0.00 | 0.00 | 0.00 | 0.00 | 0.00 | 0.00 | 0.00 | 0.00 | 0.00 | 0.00 | 0.31 | 4.94 |
| Acetilenics | 0.00 | 0.00 | 0.03 | 0.00 | 0.04 | 0.00 | 0.04 | 0.00 | 0.00 | 0.00 | 0.00 | 0.00 |
| Total | 288.75 | 100.00 | 1974.29 | 100.00 | 2944.16 | 100.00 | 2930.94 | 100.00 | 7.00 | 100.00 | 6.22 | 100.00 |

TABLE 2

| | Stream | | | | | | | | | | | |
|---|---|---|---|---|---|---|---|---|---|---|---|---|
| | 1 | | 2 | | 3 | | 4 | | 5 | | 6 | |
| | g/hr | % wt | g/hr | % wt | g/hr | % wt | g/hr | % wt | g/hr | % wt | g/hr | % wt |
| Hydrogen | 0.00 | 0.00 | 2.86 | 70.48 | 0.00 | 0.00 | 0.00 | 0.00 | 0.40 | 0.48 | 0.00 | 0.00 |
| C3 | 0.38 | 0.03 | 1.20 | 29.52 | 0.38 | 0.01 | 0.53 | 0.01 | 1.05 | 1.27 | 0.73 | 0.38 |
| Isobutane | 54.75 | 4.89 | 0.00 | 0.00 | 54.75 | 1.48 | 52.71 | 1.46 | 2.04 | 2.47 | 72.36 | 37.57 |
| Isobutene | 0.68 | 0.06 | 0.00 | 0.00 | 1.89 | 0.05 | 1.83 | 0.05 | 0.06 | 0.07 | 0.29 | 0.15 |
| Butene-1 | 421.09 | 37.61 | 0.00 | 0.00 | 1031.27 | 27.89 | 962.17 | 26.58 | 27.82 | 33.68 | 101.45 | 52.68 |
| Butadiene | 19.14 | 1.71 | 0.00 | 0.00 | 21.48 | 0.58 | 0.24 | 0.01 | 0.00 | 0.00 | 0.04 | 0.02 |
| n-butane | 199.00 | 17.78 | 0.00 | 0.00 | 507.44 | 13.72 | 538.10 | 14.87 | 12.50 | 15.13 | 4.14 | 2.15 |
| t-butene-2 | 231.69 | 20.70 | 0.00 | 0.00 | 1250.60 | 33.82 | 1241.75 | 34.31 | 26.38 | 31.94 | 10.46 | 5.43 |
| c-butene-2 | 187.73 | 16.77 | 0.00 | 0.00 | 825.21 | 22.31 | 822.21 | 22.72 | 12.35 | 14.95 | 3.12 | 1.62 |
| C5+ | 0.00 | 0.00 | 0.00 | 0.00 | 0.00 | 0.00 | 0.00 | 0.00 | 0.00 | 0.00 | 0.00 | 0.00 |
| Acetilenics | 5.06 | 0.45 | 0.00 | 0.00 | 5.10 | 0.14 | 0.04 | 0.00 | 0.00 | 0.00 | 0.00 | 0.00 |
| Total | 1119.52 | 100.00 | 4.06 | 100.00 | 3698.12 | 100.00 | 3619.58 | 100.00 | 82.59 | 100.00 | 192.59 | 100.00 |

| | Stream | | | | | | | | | | | |
|---|---|---|---|---|---|---|---|---|---|---|---|---|
| | 7 | | 8 | | 9 | | 10 | | 11 | | 12 | |
| | g/hr | % wt | g/hr | % wt | g/hr | % wt | g/hr | % wt | g/hr | % wt | g/hr | % wt |
| Hydrogen | 0.00 | 0.00 | 0.00 | 0.00 | 0.00 | 0.00 | 0.00 | 0.00 | 0.00 | 0.00 | 0.00 | 0.00 |
| C3 | 0.00 | 0.00 | 0.00 | 0.00 | 0.00 | 0.00 | 1.26 | 0.03 | 0.38 | 0.03 | 0.88 | 0.03 |
| Isobutane | 0.18 | 0.01 | 0.18 | 0.02 | 0.00 | 0.00 | 125.07 | 3.28 | 37.52 | 3.28 | 87.55 | 3.28 |
| Isobutene | 1.82 | 0.05 | 1.66 | 0.23 | 0.16 | 0.01 | 2.12 | 0.06 | 0.64 | 0.06 | 1.48 | 0.06 |
| Butene-1 | 958.24 | 28.80 | 733.25 | 99.36 | 225.00 | 8.69 | 1063.62 | 27.90 | 319.09 | 27.90 | 744.54 | 27.90 |
| Butadiene | 0.24 | 0.01 | 0.20 | 0.03 | 0.04 | 0.00 | 0.28 | 0.01 | 0.08 | 0.01 | 0.20 | 0.01 |
| n-butane | 310.36 | 9.33 | 1.21 | 0.16 | 309.15 | 11.94 | 542.25 | 14.22 | 162.67 | 14.22 | 379.57 | 14.22 |
| t-butene-2 | 1237.13 | 37.18 | 1.44 | 0.19 | 1235.70 | 47.72 | 1252.21 | 32.85 | 375.66 | 32.85 | 876.55 | 32.85 |
| c-butene-2 | 819.16 | 24.62 | 0.00 | 0.00 | 819.16 | 31.64 | 825.33 | 21.65 | 247.60 | 21.65 | 577.73 | 21.65 |
| C5+ | 0.00 | 0.00 | 0.00 | 0.00 | 0.00 | 0.00 | 0.00 | 0.00 | 0.00 | 0.00 | 0.00 | 0.00 |
| Acetilenics | 0.04 | 0.00 | 0.00 | 0.00 | 0.04 | 0.00 | 0.04 | 0.00 | 0.01 | 0.00 | 0.03 | 0.00 |
| Total | 3327.18 | 100.00 | 737.94 | 100.00 | 2589.24 | 100.00 | 3812.17 | 100.00 | 1143.65 | 100.00 | 2668.52 | 100.00 |

TABLE 2-continued

| | Stream | | | | | | | | | | | |
|---|---|---|---|---|---|---|---|---|---|---|---|---|
| | 13 | | 14 | | 15 | | 16 | | 17 | | 18 | |
| | g/hr | % wt | g/hr | % wt | g/hr | % wt | g/hr | % wt | g/hr | % wt | g/hr | % wt |
| Hydrogen | 0.00 | 0.00 | 0.00 | 0.00 | 0.00 | 0.00 | 0.00 | 0.00 | 0.00 | 0.00 | 0.00 | 0.00 |
| C3 | 0.53 | 0.18 | 0.35 | 0.01 | 0.73 | 0.02 | 0.00 | 0.00 | 0.00 | 0.00 | 0.00 | 0.00 |
| Isobutane | 52.53 | 17.96 | 35.02 | 1.47 | 72.54 | 2.06 | 0.00 | 0.00 | 0.00 | 0.00 | 0.00 | 0.00 |
| Isobutene | 0.01 | 0.00 | 1.48 | 0.06 | 2.11 | 0.06 | 1.21 | 0.05 | 0.01 | 0.16 | 0.00 | 0.01 |
| Butene-1 | 3.93 | 1.34 | 740.61 | 31.17 | 1059.70 | 30.11 | 610.18 | 23.66 | 4.23 | 83.42 | 0.17 | 3.04 |
| Butadiene | 0.00 | 0.00 | 0.20 | 0.01 | 0.28 | 0.01 | 2.34 | 0.09 | 0.00 | 0.00 | 0.00 | 0.00 |
| n-butane | 227.74 | 77.89 | 151.83 | 6.39 | 314.50 | 8.94 | 308.44 | 11.96 | 0.26 | 5.12 | 0.45 | 8.04 |
| t-butene-2 | 4.62 | 1.58 | 871.92 | 36.70 | 1247.59 | 35.45 | 1018.91 | 39.51 | 0.44 | 8.64 | 2.32 | 41.67 |
| c-butene-2 | 3.05 | 1.04 | 574.68 | 24.19 | 822.28 | 23.36 | 637.48 | 24.72 | 0.13 | 2.65 | 2.36 | 42.34 |
| C5+ | 0.00 | 0.00 | 0.00 | 0.00 | 0.00 | 0.00 | 0.00 | 0.00 | 0.00 | 0.00 | 0.27 | 4.90 |
| Acetilenics | 0.00 | 0.00 | 0.03 | 0.00 | 0.04 | 0.00 | 0.04 | 0.00 | 0.00 | 0.00 | 0.00 | 0.00 |
| Total | 292.40 | 100.00 | 2376.12 | 100.00 | 3519.77 | 100.00 | 2578.60 | 100.00 | 5.07 | 100.00 | 5.58 | 100.00 |

We claim:

1. Integrated process for the production of butene-1 which comprises:
    a) feeding a fresh feed of a $C_4$ hydrocarbon stream, consisting essentially of linear butenes, butanes and, optionally, butadiene together with a recycled stream rich in butene-1 and optionally containing traces of butadiene, to a selective hydrogenation section of butadiene and optionally acetylenic compounds;
    b) feeding the hydrogenated stream basically without butadiene and acetylenic compounds to a separation section of butene-1 to obtain a stream consisting of high purity butene-1 (>99%) and a remaining hydrocarbon stream consisting essentially of paraffins and olefins (butene-1 and butenes-2);
    c) sending the remaining hydrocarbon stream, or a fraction thereof, in a vapour phase to a molecular sieve separation section for the separation of the paraffins (consisting essentially of butanes) from the olefins (consisting essentially of butenes 1 and 2), the recovery of the olefins and the purge of the paraffins;
    d) sending the hydrocarbon stream containing the recovered olefins, together with an optional fraction not fed in step (c), to a bond isomerization section for the transformation of the cis and trans butenes-2 to butene 1;
    e) recycling the isomerized stream to the selective hydrogenation section (a) after mixing with the fresh feed $C_4$ hydrocarbon stream.

2. Process according to claim 1, wherein in the selective hydrogenation section the acetylenic compounds, optionally present in the fresh feed, are eliminated and the butadiene is transformed to linear butenes.

3. Process according to claim 1, wherein the separation of the butene-1 is carried out by fractional distillation.

4. Process according to claim 3, wherein the separation of butene-1 is carried out with two distillation columns arranged in series, in the first of which a stream consisting essentially of isobutane (isobutane stream) is separated at the top whereas in the second, fed with the bottom product of the first, butene-1 with a purity of more than 99% is obtained as top product and a stream rich in residual n-butane, butene-2, cis and trans, and containing butene-1 (butene stream), as bottom products.

5. Process according to claim 3, wherein the separation of the butene-1 is carried out with two distillation columns arranged in series, in the first column of which the butene stream is discharged at the bottom whereas in the second column, fed with the top product of the first, the high purity butene-1 is taken at the bottom, the isobutane stream being discharged at the top.

6. Process according to claim 1, wherein a fraction of remaining hydrocarbon stream of more than 5% by weight of the total stream available is sent to the molecular sieve separation section.

7. Process according to claim 1, wherein the molecular sieves are of the zeolite type capable of having selectivity with respect to the double olefinic bond.

8. Process according to claim 7, wherein the molecular sieves are selected from those having the general formula (I):

$$(Cat_{2/n}O)_x Me_2O_3(SiO_2)_y \qquad (I)$$

wherein:
    Cat represents a cation with a valence of "n", interchangeable with calcium (Ca),
    x is a number between 0.7 and 1.5;
    Me represents boron or aluminium; and
    y is a number between 0.8 and 200.

9. Process according to claim 7, wherein the molecular sieves are zeolites of the X and Y type with a particle size of between 0.1 and 3 mm.

10. Process according to claim 7, wherein the selectivity ratios olefins/paraffins of the zeolites are between 3 and 12.

11. Process according to claim 7, wherein the separation of the aliphatic hydrocarbons in step (c) is carried out in a vapour phase at a temperature of between 20 and 180° C., and a pressure of between 1 and 10 absolute bars.

12. Process according to claim 7, wherein the recovery of the olefins in step (c) is carried out by elution of the molecular sieves with a desorbing agent in a vapour phase and subsequent rectification of the mixture thus obtained.

13. Integrated process for the production of butene-1 which comprises:
    a') feeding a fresh feed of a $C_4$ hydrocarbon stream, consisting essentially of linear butenes, butanes and, optionally, butadiene, as well as optional traces of acetylenic compounds, together with a recycled stream rich in butene-1 and optionally containing traces of butadiene, to a selective hydrogenation section of butadiene and optional acetylenic compounds;
    b') sending the hydrogenated hydrocarbon stream, or a fraction thereof, in a vapour phase to a molecular sieve separation section for the separation of the paraffins (consisting essentially of butanes) from the olefins (consisting essentially of butenes 1 and 2), the recovery of the olefins and the purge of the paraffins;

c') sending the hydrocarbon stream containing the recovered olefins, together with an optional fraction not fed in step (b'), to a separation section of butene-1 to obtain a stream consisting of high purity butene-1 (>99%) and a remaining hydrocarbon stream consisting essentially of paraffins and olefins (butene-1 and butenes-2);

d') sending the remaining hydrocarbon stream to a bond isomerization section for the transformation of the cis and trans butenes-2 to butene-1;

e') recycling the isomerized stream to the selective hydrogenation section (a') after mixing with the fresh feed $C_4$ hydrocarbon stream.

14. Process according to claim 13, wherein the separation section of the butene-1 consists of a fractional distillation unit operating with two distillation columns arranged in series.

15. Process according to claim 13 which comprises:

i) feeding a fresh feed of a $C_4$ hydrocarbon stream, consisting essentially of linear butenes, butanes and, optionally, butadiene, as well as optionally traces of acetylenic compounds, together with a recycled stream rich in butene-1 and optionally containing traces of butadiene, to a selective hydrogenation section of butadiene and optionally acetylenic compounds;

ii) sending the hydrogenated hydrocarbon stream, or a fraction thereof, in a vapour phase to a molecular sieve separation section for the separation of the paraffins (consisting essentially of butanes) from the olefins (consisting essentially of butenes 1 and 2), the recovery of the olefins and the purge of the paraffins;

iii) sending the hydrocarbon stream containing the recovered olefins, together with an optional fraction not fed in step (ii), to a first column of a separation section of butene-1, the latter consisting of two distillation columns arranged in series;

iv) recycling the stream at the top of the first column of step (iii), consisting essentially of isobutane and butene-1, to the molecular sieve separation section (ii) whereas the stream at the bottom feeds the second distillation column;

v) discharging from the top of the second column a stream consisting essentially of high purity butene-1 (>99%) and sending the bottom stream of the second column, consisting essentially of butenes-2, to a bond isomerization section for the transformation of the cis and trans butenes-2 to butene-1;

vi) recycling the isomerized stream to the selective hydrogenation section (i) after mixing with the fresh feed $C_4$ hydrocarbon stream.

16. Process according to claim 15, wherein a butene stream is discharged from the bottom of a first column and high purity butene-1 is obtained from the bottom of a second column and isobutane is discharged from the top of the second column.

17. Process according to claim 16, comprising:

I) feeding a fresh feed of a $C_4$ hydrocarbon stream, consisting essentially of linear butenes, butanes and, optionally, butadiene, as well as optional traces of acetylenic compounds, together with a recycled stream rich in butene-1 and optionally containing traces of butadiene, to a selective hydrogenation section of butadiene and optionally acetylenic compounds;

II) sending the hydrogenated hydrocarbon stream, or a fraction thereof, in a vapour phase to a molecular sieve separation section for the separation of the paraffins (consisting essentially of butanes) from the olefins (consisting essentially of butenes 1 and 2), the recovery of the olefins and the purge of the paraffins;

III) sending the hydrocarbon stream containing the recovered olefins, together with an optional fraction not fed in step (II), to a first column of a separation section of butene-1, the latter consisting of two distillation columns arranged in series;

IV) sending the stream at the bottom of the first column of step (III), consisting essentially of butenes-2, to a bond isomerization section for the transformation of the cis and trans butenes-2 to butene-1 whereas the stream at the top feeds the second distillation column;

V) discharging from the bottom of the second column a stream consisting of high purity butene-1 (>99%) and sending the top stream of the second column, consisting essentially of isobutane and butene-1, to the molecular sieve separation section (II);

VI) recycling the isomerized stream to the selective hydrogenation section (I) after mixing with the fresh feed $C_4$ hydrocarbon stream.

18. The process according to claim 8, wherein Cat is selected from the group consisting of sodium, lithium, potassium and magnesium.

19. The process according to claim 11, wherein the temperature is between 70° C. and 140° C.

20. Process according to claim 8, wherein y is a number between 1.3 and 4.

* * * * *